(12) United States Patent
Skiba et al.

(10) Patent No.: US 6,908,473 B2
(45) Date of Patent: Jun. 21, 2005

(54) TISSUE ANCHORING DEVICES, BIOLOGICAL VESSEL SUSPENDING DEVICES AND SYSTEMS AND METHODS UTILIZING SAME

(76) Inventors: Jeffry B. Skiba, 1990 E. Mt. Lemmon Hwy., Oracle, AZ (US) 85623; William E. Crisp, 6051 Cactus Wren Dr., Paradise Valley, AZ (US) 85253; Ran Oren, Kibbutz Gaaton, 25 130 Doar Na Oshrat (IL)

(*) Notice: Subject to any disclaimer, the term of this patent is extended or adjusted under 35 U.S.C. 154(b) by 631 days.

(21) Appl. No.: 09/815,003

(22) Filed: Mar. 23, 2001

(65) Prior Publication Data

US 2001/0039423 A1 Nov. 8, 2001

Related U.S. Application Data

(60) Provisional application No. 60/197,099, filed on Apr. 14, 2000.

(51) Int. Cl.⁷ .............................................. A61B 17/04
(52) U.S. Cl. ........................ 606/198; 606/151; 600/29
(58) Field of Search ........................................ 600/29

(56) References Cited

U.S. PATENT DOCUMENTS

| | | | | |
|---|---|---|---|---|
| 3,903,894 A | * | 9/1975 | Rosen et al. | 600/31 |
| 3,909,894 A | * | 10/1975 | Muller | 29/25.42 |
| 4,556,050 A | * | 12/1985 | Hodgson et al. | 600/30 |
| 4,708,140 A | * | 11/1987 | Baron | 606/158 |
| 5,019,032 A | * | 5/1991 | Robertson | 600/29 |
| 5,041,093 A | * | 8/1991 | Chu | 604/104 |
| 5,041,129 A | | 8/1991 | Hayhurst et al. | |
| 5,112,344 A | | 5/1992 | Petros | |
| 5,114,398 A | * | 5/1992 | Trick et al. | 600/29 |
| 5,183,464 A | * | 2/1993 | Dubrul et al. | 606/198 |
| 5,269,809 A | | 12/1993 | Hayhurst et al. | |
| 5,707,357 A | * | 1/1998 | Mikhail et al. | 604/167.03 |
| 5,792,042 A | * | 8/1998 | Cohen et al. | 600/29 |
| 5,899,909 A | | 5/1999 | Claren et al. | |

\* cited by examiner

*Primary Examiner*—Gary Jackson
(74) *Attorney, Agent, or Firm*—G. E. Ehrlich (1995) Ltd.

(57) ABSTRACT

An elastic suspension device is disclosed. The elastic suspension device includes an element including an elastic connector and at least one anchor at an end portion of the connector, the at least one anchor is designed for anchoring the elastic connector to a tissue.

21 Claims, 7 Drawing Sheets

TISSUE ANCHORING DEVICES, BIOLOGICAL VESSEL SUSPENDING DEVICES AND SYSTEMS AND METHODS UTILIZING SAME

This application claims priority from now abandoned U.S. Provisional Patent Application No. 60/197,099, filed Apr. 14, 2000.

FIELD AND BACKGROUND OF THE INVENTION

The present invention relates to tissue anchoring devices and biological vessel suspending devices and to systems and methods utilizing same, which can be used, for example, in treating urinary incontinence associated with abnormal bladder positioning.

Urinary incontinence is characterized by the involuntary loss of urine in individuals. Urinary incontinence affects approximately 13 million people in the United States alone, 85% of them women. Urinary incontinence can be caused by physical stress (stress incontinence) typically brought on by heavy object lifting, coughing, laughing or sneezing, an overactive bladder (typically referred to as urge incontinence) or by an uncontrollable slow leak which is termed flow incontinence, and which is often experienced when complete bladder emptying can not be achieved by an individual. Additional but less common types of urinary incontinence include functional incontinence and unconscious or reflex incontinence.

Of the above causes for urinary incontinence, stress incontinence and urge incontinence are considered the most prevalent. Stress incontinence can be caused by anatomic abnormalities in the positioning of the bladder or bladder neck or by sphincter dysfunction. Urine loss occurs when the intravesical pressure (i.e., the pressure within the urinary bladder) exceeds, even by a small amount, the maximum urethral pressure (i.e., the pressure on the urethra to maintain closure). While the problem of stress incontinence occurs in both men and women, it predominantly occurs in women of childbearing age and beyond.

There are several methods and devices which can be used to alleviate involuntary loss of urine in people suffering from incontinence. Surgery is perhaps the most desirable method in cases of severe incontinence in younger patients. The surgical alternative often involves a procedure whereby the bladder neck is suspended such that the bladder assumes a normal position.

For severe cases of stress incontinence, the surgeon may secure the bladder with a wide sling positioned under the urethra. Such a sling supports the bladder and in addition compresses the bottom of the bladder and the top of the urethra, further preventing leakage.

Abdominal Suspension Procedures

One abdominal suspension procedure is the Marshall Marchetti Krantz (MMK) procedure which is still offered in many medical centers throughout the United States although it is no longer the method of choice.

In the MMK procedure, the bladder neck and urethra are separated from the back surface of the pubic bone. Sutures are placed on either side of the urethra and bladder neck, which are then elevated to a functional position. The free ends of the sutures are anchored to the surrounding cartilage and pubic bone.

The Burch procedure, also known as Burch colposuspension (vaginal suspension), is often performed in conjunction with an invasive surgical procedure such as abdominal hysterectomy (removal of the uterus). During the suspension procedure, sutures are placed laterally (sideways), thus avoiding urethral obstruction and allowing the physician to repair any small cystoceles that may be present. The bladder neck and urethra are separated from the back surface of the pubic bone and the bladder neck is then elevated via lateral sutures that pass through the vagina and Cooper's (pubic) ligaments. The vaginal wall and ligaments are brought together without tension, and the sutures are tied.

Needle Suspension

Needle suspension procedures are simpler to perform and are less invasive than abdominal suspension procedures. Numerous types of transvaginal (through the vagina) needle suspension procedures are known in the art.

In transvaginal needle suspension procedures, sutures are placed blindly through the pubic skin or via a vaginal incision into the anchoring tissues on each side of the bladder neck. The bladder neck is then supported by the sutures, which are tied to the fascia (fibrous tissue) or the pubic bone. Operative times and recovery periods are typically shorter in needle suspension techniques as compared to abdominal suspension procedures.

To enhance tissue anchoring, some needle suspension techniques employ bone anchors such as those provided by the Vesica™ and Intac/Infast™ bladder suspension kits.

Sling Procedures

Patients with severe stress incontinence and intrinsic sphincter deficiency (Type III SUI or weakening of the urethra muscle) may not be treatable via the suspension procedures described hereinabove. Such individuals are good candidates for a pubovaginal sling procedure, which can create the urethral compression necessary to achieve bladder control.

This technique involves the creation of a sling from a strip of tissue taken from the patient's abdominal fascia (fibrous tissue); occasionally, surgeons use a synthetic sling, although urethral erosion appears to be more common when synthetic slings are used.

The strip of fascia is obtained via an incision above the pubic bone. Another incision is made in the front of the vaginal wall, through which the surgeon can grasp the sling and adjust its tension around the bladder neck. The sling is secured in place by sutures which are loosely tied to each other above the incision in the pubic fascia, thus providing a hammock for the bladder neck to rest in.

The pubovaginal sling procedure generally results in high success rates, with bladder control lasting more than 10 years, although complications such as accidental bladder injury, wound infections and prolonged urinary retention severely limit the effectiveness of this technique.

The Vesica™ sling procedure employs two small anchors which are secured into the pubic bone in order to provide stable fixation for a synthetic or natural tissue sling which functions in supporting the urethra, bladder neck and sphincter.

The Precision Tack™ transvaginal anchor system also employs bone anchors which are secured into the backside of the pubic bone via a minimally invasive procedure. These anchors are connected to a sling via sutures, which sling then functions like a hammock, to support the bladder in a functional position.

Although the above described surgical procedures provide solutions to individuals suffering from urinary incontinence, such procedures suffer from several inherent limitations as follows: (i) the use of pubic bone anchors creates a potential for osteitis-pubis; (ii) the use of slings and anchors oftentimes does not improve the intra-urethral pressure differential and as such does not address voiding problems; (iii) suspensions may create the potential for residual urine in the bladder; (iv) improper tensioning of supporting sutures may cause urethral obstruction thus making self-catheterization or additional surgical intervention necessary; (v) most of these procedures require hospitalization; and (vi) surgical procedures which utilize sutures/ anchors which are secured to soft tissue or bone do not stretch as the bladder neck angle changes during voiding thus not allowing a correct bladder neck angle when voiding and in addition create a strain upon the supported tissue which can lead to tissue damage and/or support failure.

These limitations of prior art suspension techniques are the major causes underlying a reported 50 to 60% failure rate which is observed therewith following 3 years of service.

In addition, limitations inherent to bladder neck/urethra positioning techniques used by surgeons prior to or during a surgical suspension technique often lead to bladder neck mis-positioning and reduced bladder function.

There is thus a widely recognized need for, and it would be highly advantageous to have, a tissue anchoring device and a biological vessel suspending device which can be utilized for bladder suspension while being devoid of the above limitations. In addition, there is also a widely recognized need for, and it would be also highly advantageous to have, a bladder positioning assembly and a method utilizing same which can be used to correctly position the bladder neck and/or urethra prior to a surgical suspension thereof.

SUMMARY OF THE INVENTION

According to one aspect of the present invention there is provided a tissue anchoring device, comprising an element including a connector and at least one inflatable anchor at an end portion of the connector, when inflated the at least one inflatable anchor is designed for anchoring the connector to a tissue.

According to another aspect of the present invention there is provided a tissue anchoring system comprising: (a) a tissue anchoring device including an element having a connector and at least one inflatable anchor at an end portion of the connector, when inflated the at least one inflatable anchor is designed for anchoring the connector to a tissue; and (b) a guide being detachably attached to the tissue anchoring device, the guide being for inserting and positioning the tissue anchoring device within the tissue.

According to yet another aspect of the present invention there is provided a tissue anchoring system comprising: (a) at least one tissue anchoring device including an element having a connector and at least one inflatable anchor at an end portion of the connector, when inflated the at least one inflatable anchor is designed for anchoring the connector to a tissue; and (b) a biological vessel suspending device being connectable to the at least one tissue anchoring device.

According to further features in preferred embodiments of the invention described below, at least a portion of the element is designed and constructed for dampening a pulling force exerted thereon.

According to still further features in the described preferred embodiments the inflatable anchor is designed and constructed for dampening a pulling force exerted on the element.

According to still another aspect of the present invention there is provided a tissue anchoring device, comprising an element including a connector and at least one anchor being designed for engaging a tissue at an end portion of the connector, at least a portion of the element being designed and constructed for dampening a pulling force exerted thereon.

According to an additional aspect of the present invention there is provided a tissue anchoring system comprising: (a) a tissue anchoring device including an element having a connector and at least one anchor being designed for engaging a tissue at an end portion of the connector, at least a portion of the element being designed and constructed for dampening a pulling force exerted thereon; and (b) a guide being detachably attached to the tissue anchoring device, the guide being for inserting and positioning the tissue anchoring device within the tissue.

According to yet an additional aspect of the present invention there is provided a tissue anchoring system comprising: (a) at least one tissue anchoring device including an element having a connector and at least one anchor being designed for engaging a tissue at an end portion of the connector, at least a portion of the element being designed and constructed for dampening a pulling force exerted thereon; and (b) a biological vessel suspending device being connectable to the at least one tissue anchoring device.

According to still further features in the described preferred embodiments the at least one anchor is an inflatable anchor designed for anchoring the connector to the tissue when inflated.

According to still further features in the described preferred embodiments at least a portion of the connector is composed of an elastic material capable of elastically complying to a pulling force exerted upon the element.

According to still further features in the described preferred embodiments the connector includes a spring capable of elastically complying to a pulling force exerted upon the element.

According to still an additional aspect of the present invention there is provided a biological vessel suspending device comprising a generally U-shaped element for engaging a biological vessel therein, the U-shaped element having inner walls being designed and constructed for preventing disengagement of the biological vessel from the U-shaped element.

According to still further features in the described preferred embodiments the inner walls include inflatable elements.

According to still further features in the described preferred embodiments the inner walls are formed with ridges and grooves.

According to still further features in the described preferred embodiments the inner walls are further designed and constructed capable of at least partially obstructing a flow through the biological vessel when engaged in the generally U shaped element.

According to still further features in the described preferred embodiments the biological vessel suspending device further comprising at least one connector forming a part of, or being attached to, the generally U-shaped element, the at least one connector being for connecting the biological vessel suspending device with a tissue anchoring device.

According to still further features in the described preferred embodiments a degree of inflation of the inflatable elements determines a flow through the biological vessel.

According to a further aspect of the present invention there is provided a method of suspending a biological vessel, the method comprising the step of: (a) anchoring at least one tissue anchoring device within a tissue, the at least one tissue anchoring device including an element having at least one anchor at an end portion of the connector, the at least one anchor being designed for anchoring the connector to a tissue; (b) engaging the biological vessel within a biological vessel suspending device being designed and constructed for preventing disengagement of said biological vessel therefrom; and (c) connecting the biological vessel suspending device to the at least one tissue anchoring device thereby suspending the biological vessel.

According to still further features in the described preferred embodiments the at least one anchor of the at least one tissue anchoring device is an inflatable anchor designed for anchoring the connector to a tissue when inflated.

According to still further features in the described preferred embodiments at least a portion of the element of the at least one tissue anchoring device is designed and constructed for dampening a pulling force exerted on the element by said biological vessel suspending device connected thereto.

According to still further features in the described preferred embodiments at least a portion of the element of the at least one tissue anchoring device is composed of an elastic material capable of complying to a pulling force exerted on the element by the biological vessel suspending device connected thereto.

According to still further features in the described preferred embodiments the element of the at least one tissue anchoring device includes a spring capable of complying to a pulling force exerted on the element by the biological vessel suspending device connected thereto.

According to still further features in the described preferred embodiments the inner walls of the biological vessel suspending device are further designed and constructed capable of partially obstructing a flow through the biological vessel when engaged within the generally U shaped element.

According to still further features in the described preferred embodiments the biological vessel is the urethra or the bladder neck.

According to still further features in the described preferred embodiments the inner walls include inflatable elements.

According to still further features in the described preferred embodiments the inner walls are formed with ridges and grooves.

According to still further features in the described preferred embodiments a degree of inflation of the inflatable elements determines a flow through the biological vessel.

According to a further aspect of the present invention there is provided an assembly useful for accurately positioning a bladder neck and/or urethra prior to a surgical suspension thereof, the assembly comprising: (a) at least one target marker positionable at an abdominal skin region; (b) a saddle shaped element for engaging the bladder neck or urethra; and (c) at least one connecting element being for attaching the saddle shaped element to the at least one target marker thereby positioning the saddle shaped element relative to the at least one target marker and enabling accurate positioning of the bladder neck and/or urethra when engaged by the saddle shaped element.

According to still further features in the described preferred embodiments the at least one connecting element is designed and constructed to enable modifying a distance between the at least one target marker and the saddle shaped element when interconnected thereby.

The present invention successfully addresses the shortcomings of the presently known configurations by providing a tissue anchoring device and a biological vessel supporting device, and systems and methods utilizing same for effecting tissue to tissue anchoring.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
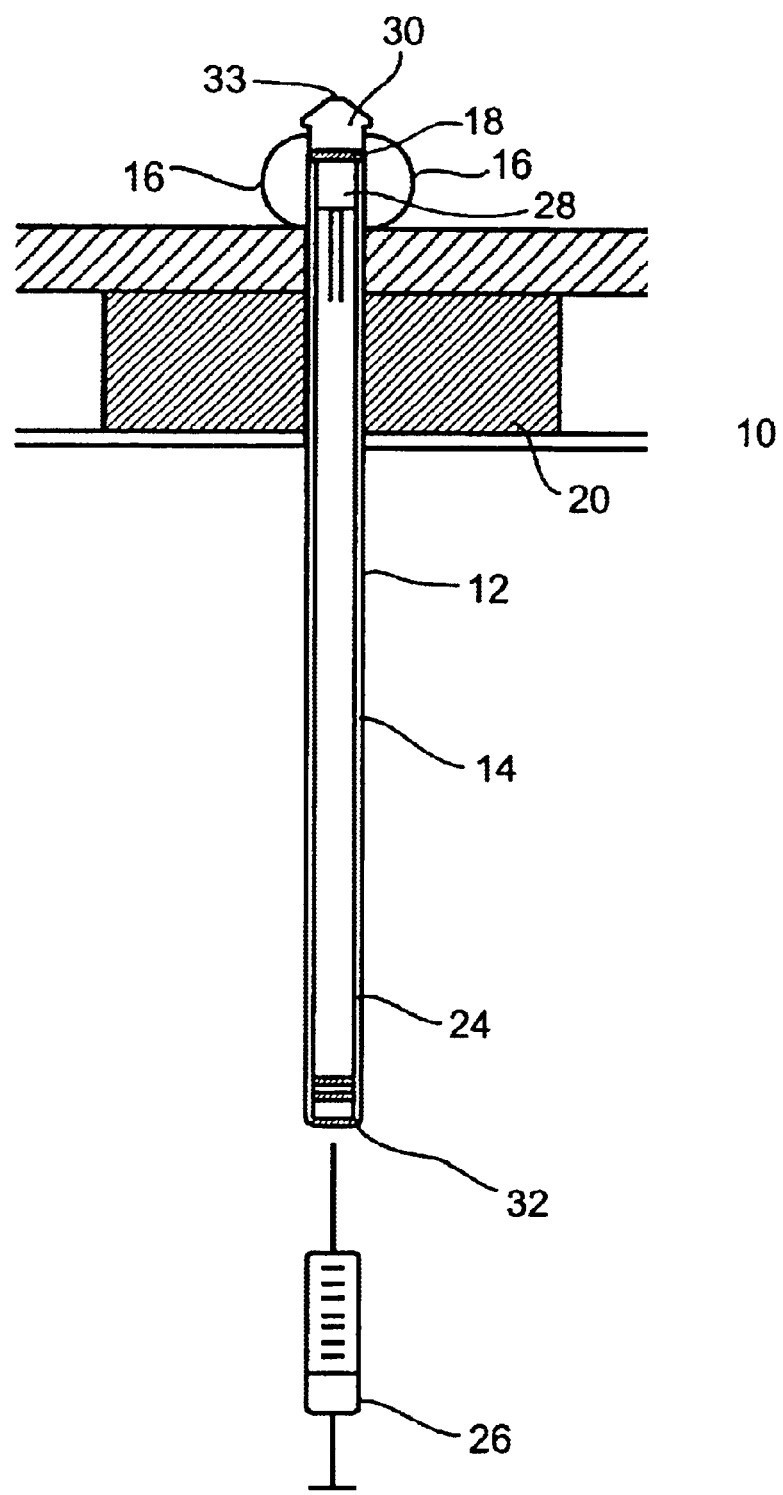
FIG. 1 illustrates a tissue anchoring device according to one embodiment of the present invention.

The present invention is of a tissue anchoring device and a biological vessel supporting device and of systems and methods utilizing same. Specifically, the present invention can be used to anchor tissue to tissue while allowing tissue compliance and reducing forces applied to the tissue, thus reducing the risk of tissue damage and/or anchoring failure.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a tissue anchoring device in accordance with the teachings of the present invention, which is referred to hereinbelow as anchoring device 10.

Device 10 includes an element 12 which includes a connector 14 and at least one inflatable anchor 16 which is attached to, or form a part of a distal portion 18 of connector 14. Preferably connector 14 is tubular in shape having a diameter ranging from several millimeters to several centimeters and having a length of several centimeters or more depending on the application of anchoring device 10 and the tissue into which it is anchored.

Anchoring device 10 is typically constructed from one or more biocompatible polymer such as that utilized in catheters or other intrabody devices and/or any biocompatible material suitable for use in implants. Preferably, the biocompatible polymer is selected so as to minimize tissue growth around anchoring device 10, since, as described in detail hereinbelow, anchoring device 10 is preferably utilized for predetermined time periods following which removal thereof is preferred.

Inflatable anchor 16 is designed for anchoring connector 14 to a tissue region 20 when inflated. Tissue region 20 can include, for example, bone or cartilage tissue, muscle tissue and/or connective tissue.

Figure 2A:
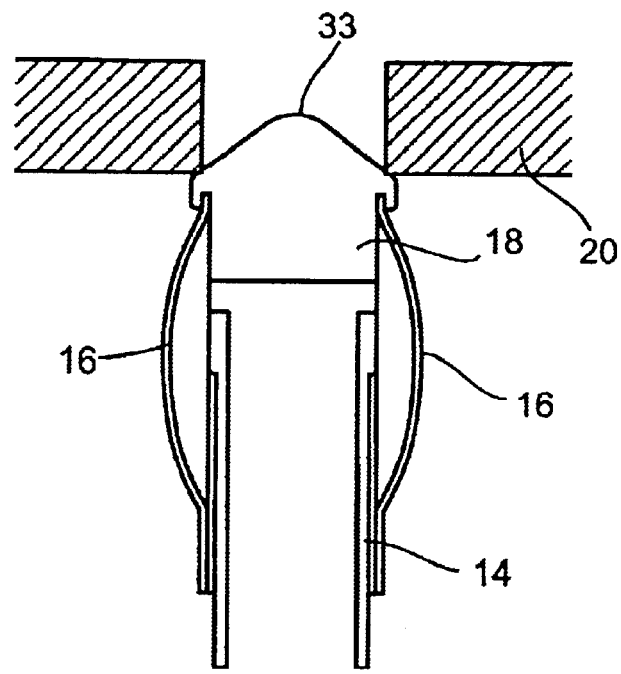
FIGS. 2a–b illustrate positioning (FIG. 2a) and anchoring (FIG. 2b) of the tissue anchoring device of FIG. 1.
Figure 2B:
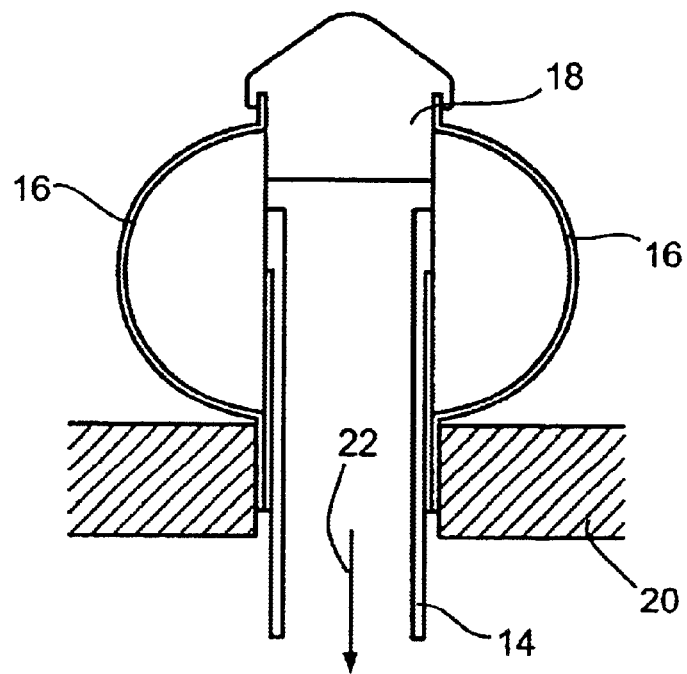

As is shown in FIGS. 2a–b, inflatable anchor 16, is inflated following insertion and positioning of anchoring device 10 into tissue region 20.

Figure 3:
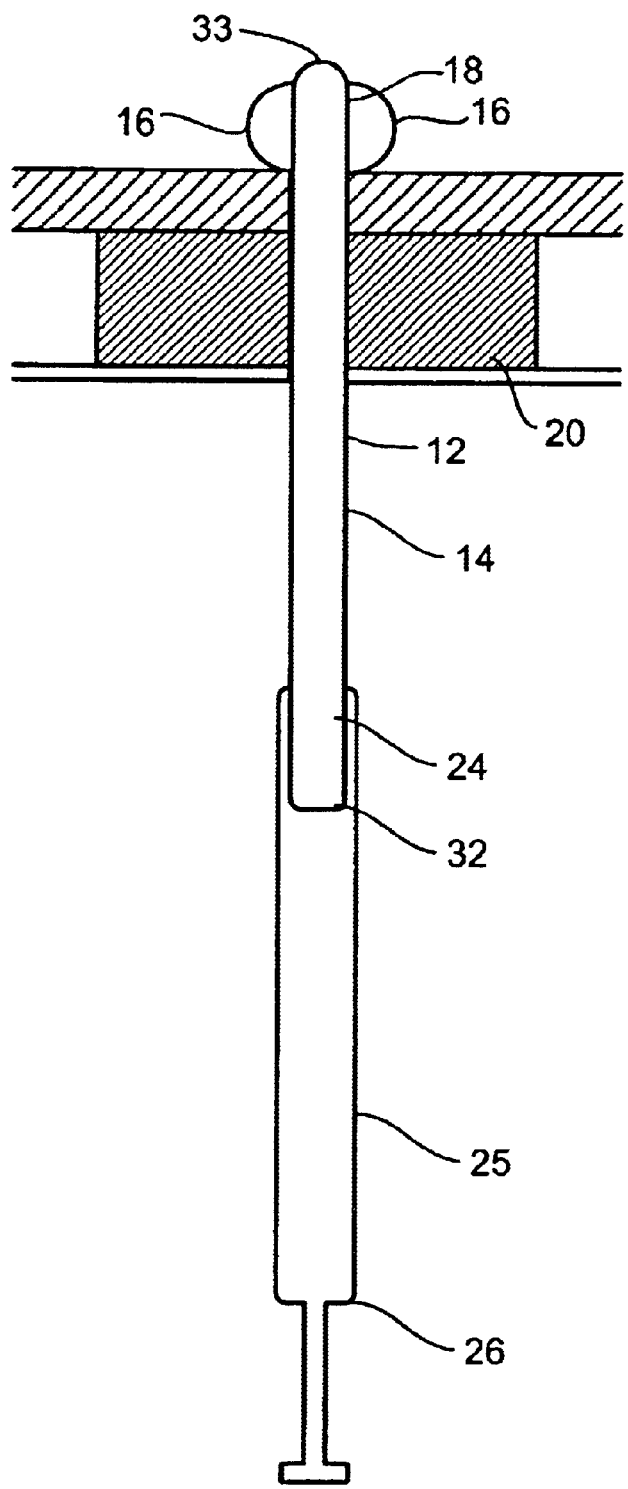
FIG. 3 illustrates the tissue anchoring device of FIG. 1 attached to a positioning guide according to the present invention.

As is shown in FIG. 3 such insertion and positioning can be facilitated by a guide 25, which is detachably attached to anchoring device 10 at a proximal portion 24 thereof.

Preferably, tissue region 20 is pierced prior to insertion of anchoring device 10 by either guide 24 which in this case includes a distal end portion adapted for this purpose, or alternatively by a medical device such as a tissue piercer, a syringe needle or the like.

Alternatively, a distal end 33 of anchoring device 10 can be designed and configured so as to facilitate self insertion thereof into tissue region 20 without a need for first piercing the tissue.

Once anchoring device 10 is positioned within tissue region 20, inflatable anchor 16 is inflated via a fluid such as air, gas, or saline, provided under pressure from, for example, via a syringe 26 (shown in FIG. 1) which, in some configurations, forms a part of guide 25.

The fluid provided from syringe 26 can be utilized to directly inflate inflatable anchor 16, or alternatively it can be utilized to drive a piston provided within distal portion 18 of anchoring device 10, which in turn forces a fluid stored within reservoir 30 into inflatable anchor 16.

In any case, upon inflation, anchor 16 assumes a protruded configuration (as shown, for example, in FIG. 2b) which prevents anchoring device 10 from being pulled out of tissue region 20.

Anchoring device 10 of the present invention can be used in tissue to tissue anchoring including for example, bone to bone, bone to soft tissue and soft tissue to soft tissue anchoring.

For example, anchoring device 10 of the present invention can be utilized in a system designed for suspending and positioning a urinary bladder, the abnormal positioning of which (descended) leads to urinary incontinence in affected individuals.

Figure 4A:
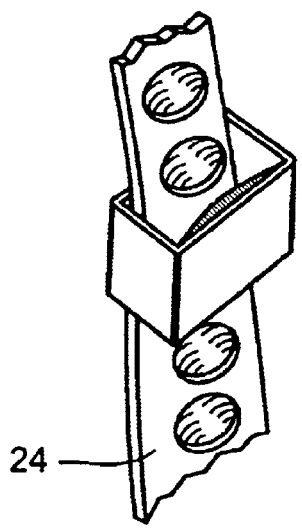
FIGS. 4a and 4b illustrate various connector ends of the tissue anchoring device of the present invention.
Figure 4B:
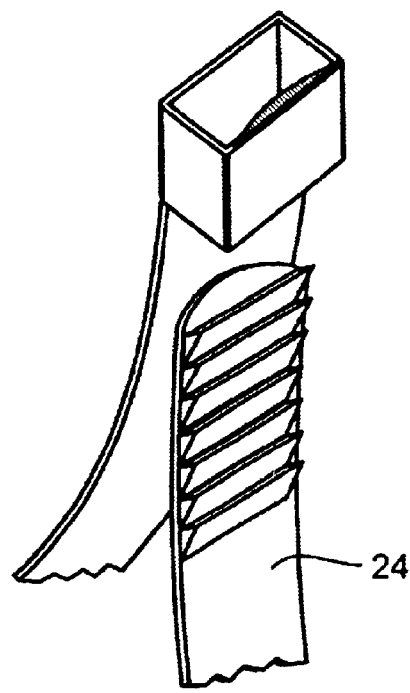

As such, connector 14 of anchoring device 10 can be adapted for directly or indirectly connecting to an intrabody organ such as a bladder or to a biological vessel connected thereto. As is specifically shown in FIGS. 4a and 4b for this purpose, proximal portion 24 of connector 14 is configured with holes, ridges and groves and/or various other elements which facilitate direct or indirect connection to, for example, slings designed for suspending a urinary bladder.

It will be appreciated that during service, especially when utilized for suspending a urinary bladder, anchoring device 10 of the present invention is subjected to considerable pulling forces resultant from movement of the suspended bladder.

Thus, according to another preferred embodiment of the present invention, connector 14 and/or inflatable anchor 16 are designed and constructed for elastically complying to a pulling force exerted on anchoring device 10 (indicated by 22 in FIG. 2b). Such elastic compliance results in dampening of the pulling force as well accommodation, features which are particularly advantageous as is further detailed hereinbelow.

As used herein, the term "elastically complying" refers to the ability to absorb (dampen) a force via an elastic structural change.

To enable such elastic compliance, at least a portion of connector 14 is fabricated from an elastic material such as silicon rubber, PEEK, ultra high molecular weigh polyethylene (UHMWPE) or Nitinol. Thus, in this case, a pulling force applied to proximal end 32 of connector 14 would be absorbed, at least in part, by elastic stretching of at least a portion of connector 14.

The elastic portion of connector 14 can be selected of a material or configuration allowing for a controlled (e.g., slow) contraction following elastic stretching. Such controlled contraction can be useful in cases where rapid contraction of the elastic portion of connector 14 can be damaging to tissues or organs.

Alternatively, such elastic compliance can be effected by a spring of a shape and composition specifically designed for body tissue implantation. Such a spring can be fabricated in a cone-like shape such that the wider end can serve as a tissue anchor while the narrower end can serve as a direct or indirect point of attachment to a sling.

Additionally or alternatively, inflatable anchor 16 can be configured such that a pulling force applied to proximal end 32 would be, at least in part, absorbed by directional and elastic compression of inflatable anchor 16 which at the same time would not substantially reduce the anchoring capabilities thereof.

In any case, such compliance/dampening features provide two important advantages. A first advantage is the considerable reduction of a force applied upon the anchoring device 10 and as such a reduced risk of tissue damage and/or anchoring failure. A second advantage lies with the directional compliance of anchoring device 10 which enables anchoring device 10 to elastically stretch. Such elastic stretching is especially important in cases where anchoring device 10 is used for suspending a bladder which requires a certain degree of accommodation to assure correct bladder neck positioning and thus function at all times.

It will be appreciated that although the use of an inflatable anchor 16 provides several inherent advantages over other anchor configurations, an anchoring device 10 employing anchors such as, but not limited to, deployable mushroom-like devices in place of inflatable anchor 16 are also envisaged by the present invention. Preferably, such anchors are configured capable of dampening a pulling force applied upon anchoring device 10.

In many surgical cases tissue such as a tendon or ligament needs to be firmly reattached to a bone from which it was detached. A typical prior art reconstruction of the area may involve the use of sutures and implantable anchors which are driven into bone providing an eyelet for reattachment of the detached tissue. Such devices are commercially available through Johnson & Johnson's Mitek division, Zimmer's Statac Product Line, and numerous other manufacturers. While these devices may provide approximation of tissue, they do not address the original compliance of the tissue and as such surgical repairs are stiff and inflexible. Surgeons opt to use absorbable sutures which are absorbed over time leaving the compliance of the site much the same as before the procedure.

Thus, anchoring device 10 of the present invention is also advantageous for use in cases where some motion in the repaired site is desired.

Figure 5A:
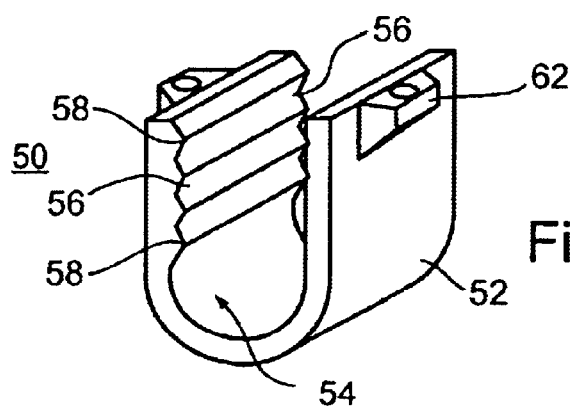
FIG. 5a illustrates a biological vessel supporting device according to one embodiment of the present invention.
Figure 5B:
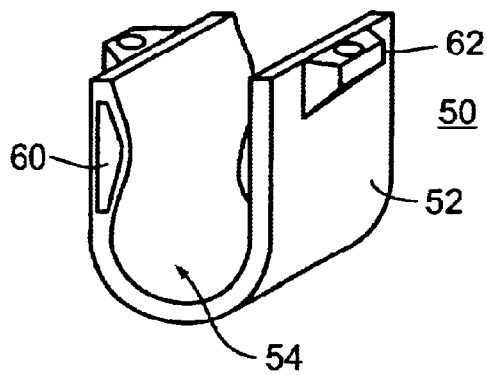
FIGS. 5b–c illustrate a biological vessel supporting device according to another embodiment of the present invention showing the inflatable vessel engagement elements in a deflated (FIG. 5b) and an inflated (FIG. 5c) configuration.

According to another aspect of the present invention and as specifically shown in FIGS. 5a–b there is provided a biological vessel suspending device which is referred to herein as suspending device 50.

Suspending device 50 includes a generally U-shaped element 52 which acts as a sling for engaging a biological vessel, such as a blood vessel or a urethra. Inner walls 54 of element 52 are designed and constructed for preventing disengagement of a biological vessel therefrom.

According to one preferred embodiment of this aspect of the present invention and as specifically shown in FIG. 5a, inner walls 54 include grooves 56 and ridges 58 which serve for grasping the biological vessel, thus preventing disengagement of the biological vessel from suspending device 50.

Figure 5C:
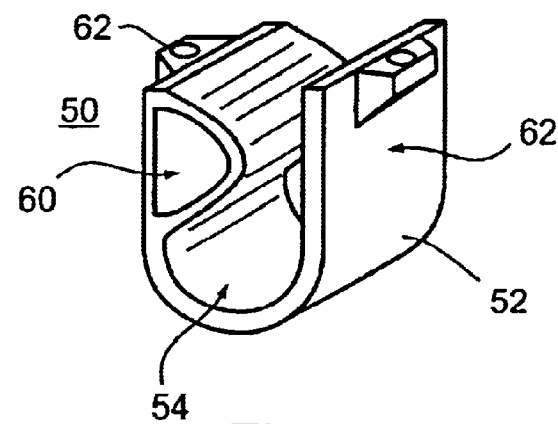

According to another preferred embodiment of this aspect of the present invention, and as specifically shown in FIGS. 5b–c, inner walls 54 include one or preferably several inflatable elements 60. Inflatable elements 60 are designed to forcibly engage the biological vessel when inflated, thus preventing disengagement of the biological vessel from suspending device 50.

In addition, inflatable elements 60 also serve for controlling the flow of biological fluid through the biological vessel. For example, inflatable elements 60 can be configured such that when inflated to a predetermined volume they compress the biological vessel so as to partially or fully constrict flow therethrough. Thus, the degree of inflation and the number of inflatable elements employed can be utilized to regulate flow through the biological vessel.

Inflation of inflatable elements 60 can be effected by direct injection of fluid, such as air or saline, into inflatable elements 60 or injection ports thereof, via, for example, a syringe. As such, the number of elements 60 inflated and the degree of inflation of each and thus the degree of constriction on the biological vessel can be effected even following implantation of suspending device 50.

By using an imaging modality, a treating physician can locate and inflate inflatable elements 60 using a mildly invasive procedure. For example, ultrasound imaging can be utilized to locate saline filled inflatable elements 60 which can then be inflated or deflated using a syringe and needle.

The use of inflatable elements 60 for engaging a biological vessel is particularly advantageous since it allows a physician to control the force applied on the vessel while at the same time control fluid flow therethrough. This is especially true when engaging a urethra for bladder repositioning in incontinence treatment since it allows a physician to safely and easily suspend the bladder while at the same time to determine fluid flow through the urethra which is most suitable for each case.

Suspending device 50 is preferably utilized in conjunction with sutures and/or tissue anchors in order to provide support to a descended bladder. Preferably, suspending device 50 is utilized in conjunction with anchoring device 10 described hereinabove.

In any case, to enable attachment to sutures or anchors, suspending device 50 includes one or more connecting elements 62 which enable direct connection to suture threads, tissue anchors and the like.

Preferably, connecting elements 62 are configured connectable with connector 14 of anchoring device 10 described hereinabove.

Thus, the present invention provides a tissue anchoring device and a biological vessel supporting device each utilizable in various bladder support techniques.

Anchoring device 10 and or suspending device 50 can be inserted and positioned using trans-vaginal procedures employing, for example, a dedicated and minimally invasive procedure.

For example, when utilized for supporting a descended bladder, one or more anchoring devices 10 are inserted into a tissue pre-pierced via a small incision made by, for example, a hypodermic needle or a sharpened tube, which can also act as guide 25 described hereinabove. Once in place, anchoring device 10 is anchored and connected to a sling such as suspending device 50 which engages a biological vessel of interest, such as the urethra. The connection tension between anchoring device 10 and the sling is then adjusted such that the bladder is supported in a natural position. In cases where urethral flow control is necessary, suspending device 50 which includes inflatable elements 60 is preferably utilized. In this case, inflatable elements 60 are inflated to a desired volume as described hereinabove to thereby set a predetermined flow rate.

In addition to the above application, suspending device 50 and in particular anchoring device 10 can be utilized for various other applications.

As a body ages and experiences the effects of gravity, tissue compliance is altered leading to changes in tissue strength and as such support. In some cases this change in tissue compliance is cosmetic, while in others it alters normal physiological function.

Thus, restoration of tissue compliance and support is another object of the present invention. For example, the present invention can be utilized in face lift, brow lift, breast lift and thigh lift procedures as well as for correcting vaginal prolapse, cystoceal, recticeal, and the like.

Thus, the present invention provides a tissue anchoring device and a biological vessel suspending and systems and methods utilizing each or both.

It will be appreciated that when utilized in bladder suspension procedures, the present invention provides numerous advantages over the prior art.

In urinary incontinence, maintenance of the bladder neck angle alone only solves a part of the problem. The bladder neck angle was originally designed to move with increased abdominal pressure which forces the urethra/bladder neck down and allows voiding of the bladder. With most prior art surgical solutions, the ability of the angle to change with abdominal pressure is lost since most utilized devices do not provide for compliance.

By enabling compliance through elastic changes, the present invention allows the bladder neck angle to move downward with increased abdominal pressure while reducing the force on the anchored tissue. This unique approach to conditioned tension closely simulates the natural function of the tissue surrounding the bladder neck/urethra.

An additional limitation which severely affects the success rate of prior art surgical suspension techniques is the inability of the surgeon to correctly position the bladder neck and/or the urethra prior to or during a surgical suspension procedure.

Figure 6:
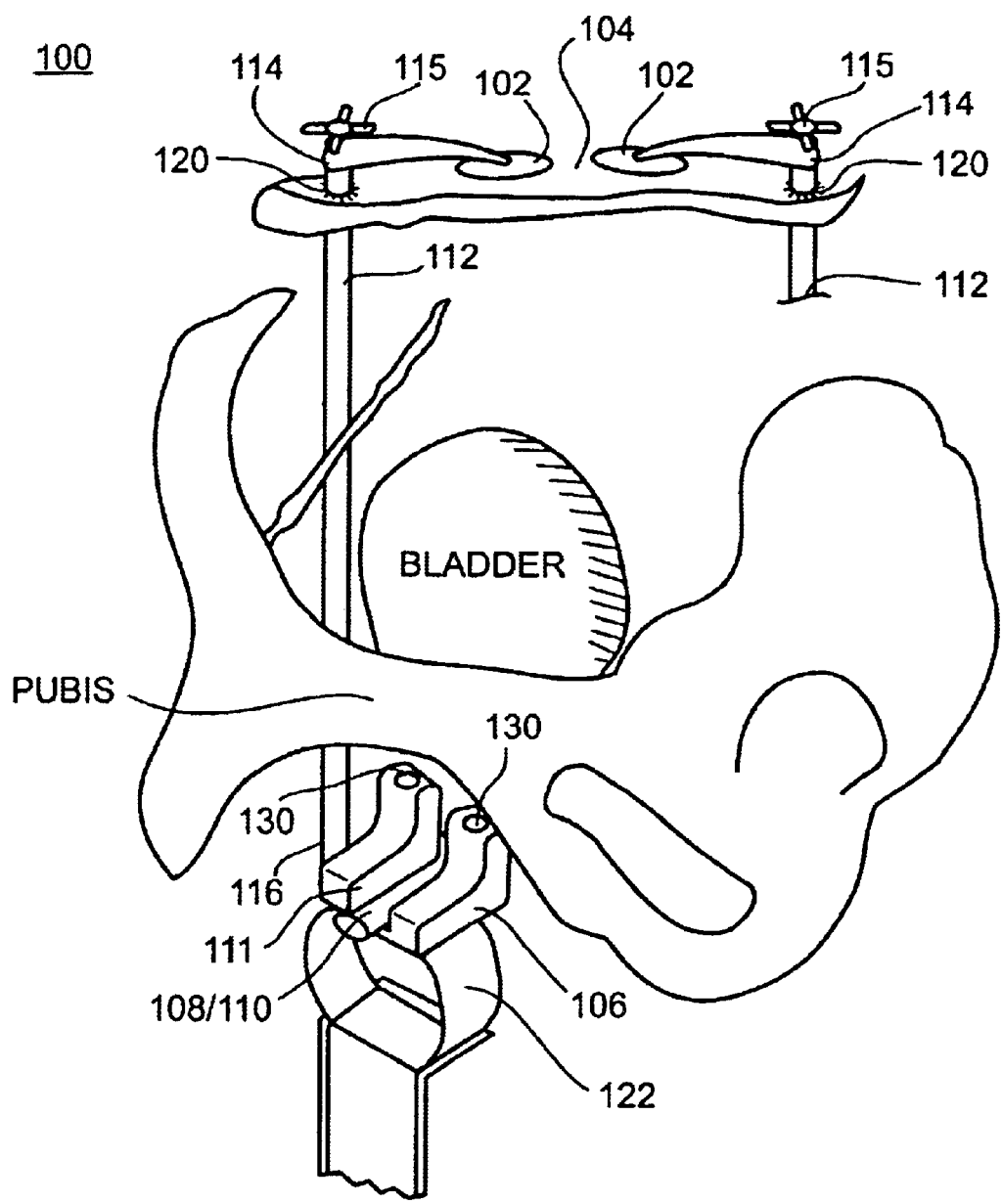
FIG. 6 is a perspective view of an assembly for positioning the bladder neck and/or urethra in preparation for a surgical suspension procedure according to the present invention as positioned in relation to the bladder, pubis and surrounding tissue.

Thus, according to another aspect of the present invention and as specifically shown in FIG. 6, there is provided an assembly useful for positioning the bladder neck and/or urethra prior to surgical suspension thereof, which is referred to herein as assembly 100.

Assembly 100 includes one or more (two are shown in FIG. 6) target markers 102 which are individually positionable upon an abdominal skin region 104. Such positioning can be effected via adhesive backing, suction or the like as long as target markers 102 remain securely fastened to skin region 104 while being easily (and preferably painlessly) detachable therefrom following bladder positioning.

Assembly 100 further includes a saddle shaped element 106 (hereinafter saddle 106) for engaging the bladder neck 108 or urethra 110. Such engagement can be effected via an engagement groove 111 optionally provided with the inflatable elements described hereinabove. Groove 111 is constructed so as to securely engage the bladder neck and/or urethra while being easily detachable therefrom when desired.

Assembly 100 also includes at least one connecting element 112 which serves for attaching saddle 106 to target marker(s) 102. Such attachment enables to position saddle 106 relative to target marker(s) 102 thus enabling accurate positioning of the bladder neck and/or urethra when engaged by the saddle shaped element.

Connecting element 112 is designed and constructed so as to enable modification/adjustment of a distance between the at least one target marker and the saddle shaped element when interconnected thereby.

For example, a target marker end 114 of connecting element 112 can be configured with an adjustment mechanism 115 (such as a screw) which can be utilized to adjust the length of connecting element 112 and as such to adjust the distance between target marker 102 and saddle 106 interconnected thereby.

Alternatively, the saddle attachment end 116 of connecting element 112 can include a plurality of saddle attachment sites 118 which enable accurate and indexed positioning of saddle 106 relative to target markers 102, thus enabling accurate positioning of the bladder neck and/or urethra.

As shown in FIG. 6, assembly 100 of the present invention can be used to position the bladder and/or urethra in the following manner.

One or more target marker(s) 102, are fixed to abdominal skin region 104 which lies directly above the pubic bone, and small abdominal incisions (indicated at 120) are made with, for example, a scalpel.

A No. 16–18 French catheter is placed in the urethra to stabilize it and to allow manipulation thereof. With a speculum 122 inserted, a small incision is made in the vaginal wall in order to expose the urethra. The incision is forced open with a retractor, the urethra is separated from the vaginal wall and saddle 106 is positioned such that the urethra is engaged by saddle 106.

Connecting element 112 is inserted via the vaginal incision and used to attach saddle 106 to target marker(s) 102 by threading end 114 of connecting element 112 through the abdominal incision (indicated at 120).

Using adjustment mechanism 115, saddle 106 and bladder neck/urethra engaged thereby are pulled towards the pubic bone (pubis) until a desired position is achieved and connecting element 112 is locked in place thus suspending the bladder/urethra at the desirable position.

Thus, assembly 100 of the present invention enables positioning of the bladder neck/urethra prior to suspension surgery, thus freeing the surgeon from having to keep the bladder neck/urethra in the correct position during a surgical procedure.

It will be appreciated that assembly 100 and the above described method of utilizing same can be used prior to any prior art surgical suspension procedure.

Preferably, the above described method is utilized with tissue anchoring device 10 and/or suspending device 50 of the present invention.

Figure 7:
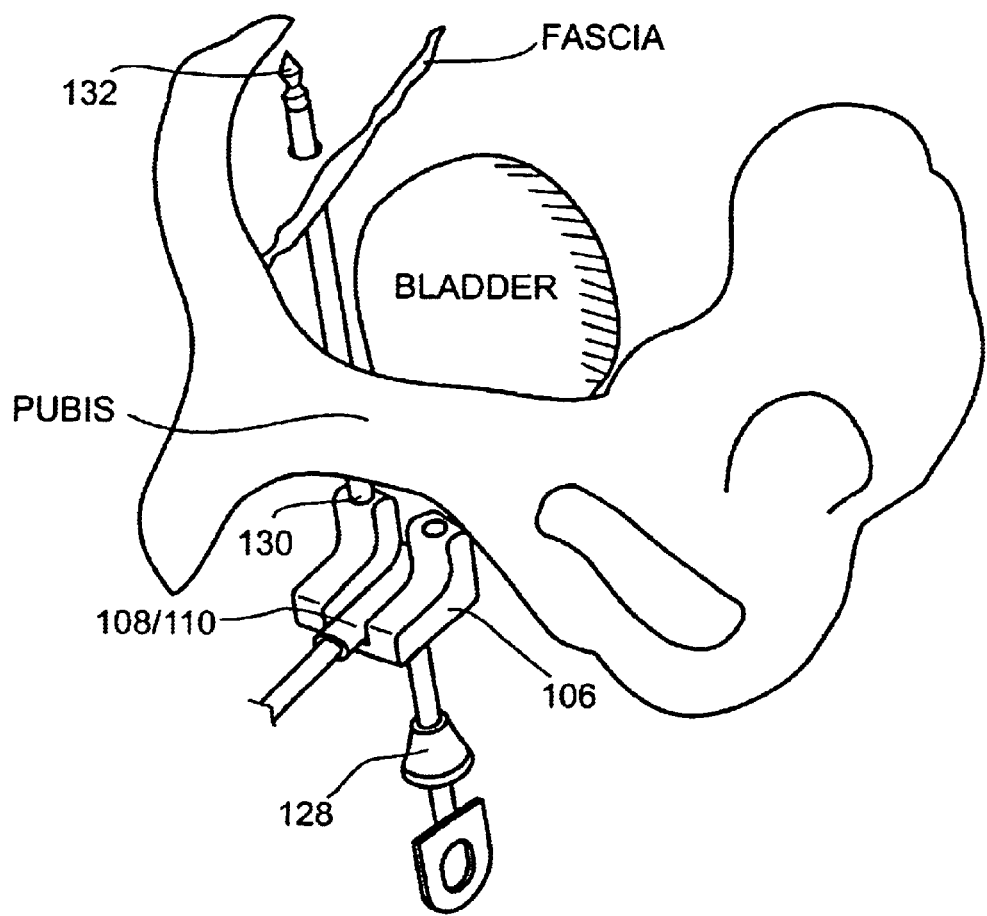
FIGS. 7–8 illustrate tissue piercing (FIG. 7) and anchor positioning (FIG. 8) as guided by the saddle shaped element of the assembly illustrated in FIG. 6.
Figure 8:
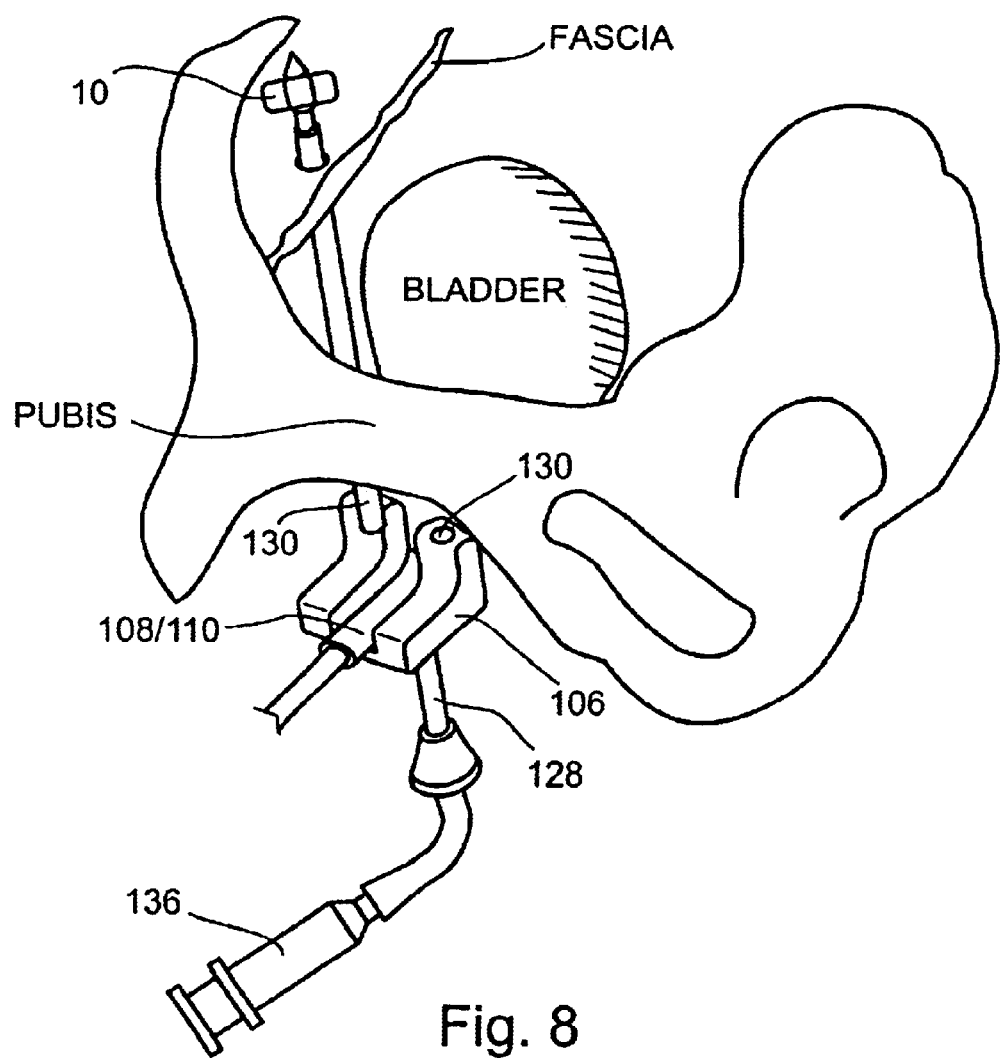

Thus, as shown in FIGS. 7–8, following bladder positioning, a guide 128 can be inserted into one of the guide bores 130 provided in saddle 106 and advanced until the urogenital diaphragm is reached (resistance of fibrous tissue is felt). The guide or a sharp piercer 132 is used to perforate the diaphragm and with the guide re-inserted or the sharp point of the guide withdrawn, tissue anchoring device 10 and preferably an attached suspending device 50 are advanced along the lower surface of the pubic bone in the retro-pubic space, until the rectus fascia (Fascia) which serves as a site for tissue anchoring is reached.

As specifically shown in FIG. 8, guide 128 (or piercer 132) is used to drive tissue anchoring device 10 (inflatable anchor) into the rectus fascia tissue and to deploy an anchor element, such as an inflatable anchor element via a syringe 136 which is connected to guide 128. Following anchoring, suspending device 50 is attached to the bladder neck or urethra and if necessary connected to anchoring device 10. It will be appreciated, that saddle 106 can be designed to also function as suspending device 50, thus negating the need to position suspending device 50 and to remove saddle 106.

Following removal of assembly 100, the elastic compliance feature of tissue anchoring device 10 and/or attached suspending device 50 ensure that correct bladder neck position is maintained at all times. In addition, such elastic compliance dampens forces applied to anchored tissues thus reducing or preventing tissue damage.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tissue anchoring system comprising:
   (a) at least one tissue anchoring device including an element having a connector and at least one inflatable anchor at an end portion of said connector, when inflated said at least one inflatable anchor is designed for anchoring said connector to a tissue; and
   (b) a biological vessel suspending device being connectable to said at least one tissue anchoring device; said biological vessel suspending device including a generally U-shaped element for engaging a biological vessel therein, said U-shaped element having inner walls being designed and constructed for preventing disengagement of said biological vessel from said U-shaped element.

2. The tissue anchoring system of claim 1, wherein said inner walls of said biological vessel suspending device include inflatable elements.

3. The tissue anchoring system of claim 1, wherein said inner walls of said biological vessel suspending device are formed with ridges and grooves.

4. A tissue anchoring system comprising:
   (a) at least one tissue anchoring device including an element having a connector and at least one anchor being designed for engaging a tissue at an end portion of said connector, at least a portion of said element being designed and constructed for dampening a pulling force exerted thereon; and
   (b) a biological vessel suspending device being connectable to said at least one tissue anchoring device; wherein said biological vessel suspending device including a generally U-shaped element for engaging a vessel therein, said U-shaped element having inner walls being designed and constructed for preventing disengagement of said biological vessel from said U-shaped element.

5. The tissue anchoring system of claim 4, wherein said at least one anchor is an inflatable anchor designed for anchoring said connector to said tissue when inflated.

6. The tissue anchoring system of claim 4, wherein at least a portion of said connector is constructed of an elastic material capable of elastically complying to said pulling force.

7. The tissue anchoring system of claim 4, wherein said connector includes a spring capable of elastically complying to said pulling force.

8. The tissue anchoring system of claim 4, wherein said inner walls of said biological vessel suspending device include inflatable elements.

9. The tissue anchoring system of claim 4, wherein said inner walls of said biological vessel suspending device are formed with ridges and grooves.

10. A method of suspending a biological vessel, the method comprising:
    (a) anchoring at least one tissue anchoring device within a tissue, said at least one tissue anchoring device including an element having at least one anchor at an end portion of said connector, said at least one anchor being designed for anchoring said connector to a tissue;
    (b) engaging the biological vessel within a biological vessel suspending device being designed and constructed for preventing disengagement of said biological vessel therefrom; and
    (c) connecting said biological vessel suspending device to said at least one tissue anchoring device thereby suspending the biological vessel.

11. The method of claim 10, wherein said at least one anchor of said at least one tissue anchoring device is an inflatable anchor designed for anchoring said connector to a tissue when inflated.

12. The method of claim 10, wherein at least a portion of said element of said at least one tissue anchoring device is designed and constructed for dampening a pulling force exerted thereon by said biological vessel suspending device connected thereto.

13. The method of claim 10, wherein at least a portion of said element of said at least one tissue anchoring device is composed of an elastic material capable of complying to a pulling force exerted on said element by said biological vessel suspending device connected thereto.

14. The method of claim 10, wherein said biological vessel suspending device is further designed and constructed capable of partially obstructing a flow through said biological vessel when engaged within said biological vessel suspending device.

15. The method of claim 10, wherein said biological vessel suspending device includes a generally U-shaped element having inner walls being designed and constructed for preventing disengagement of said biological vessel from said U-shaped element.

16. The method of claim 10, wherein the biological vessel is the urethra.

17. The method of claim 10, wherein said inner walls include inflatable elements.

18. The method of claim 17, wherein a degree of inflation of said inflatable elements determines a flow through said biological vessel.

19. The method of claim 10, wherein said inner walls are formed with ridges and grooves.

20. An assembly useful for accurately positioning a bladder neck and/or urethra prior to a surgical suspension thereof, the assembly comprising:
    (a) at least one target marker positionable at an abdominal skin region;
    (b) a saddle shaped element for engaging the bladder neck or urethra; and
    (c) at least one connecting element being for attaching said saddle shaped element to said at least one target marker thereby positioning said saddle shaped element relative to said at least one target marker and enabling accurate positioning of the bladder neck and/or urethra when engaged by said saddle shaped element.

21. The assembly of claim 20, wherein said at least one connecting element is designed and constructed to enable modifying a distance between said at least one target marker and said saddle shaped element when interconnected thereby.

* * * * *